US00PP09185P

United States Patent [19]

Van Der Meer

[11] Patent Number: Plant 9,185

[45] Date of Patent: Jul. 4, 1995

[54] HYBRID TEA ROSE PLANT NAMED 'SELVANADIUM'

[75] Inventor: Peter J. A. Van Der Meer, Carlsbad, Calif.

[73] Assignee: Terra Nigra B.V., De Kwakel, Netherlands

[21] Appl. No.: 105,357

[22] Filed: Aug. 11, 1993

[30] Foreign Application Priority Data

Dec. 15, 1992 [NL] Netherlands ..... R00 1912

[51] Int. Cl.[6] ..... A01H 5/00

[52] U.S. Cl. ..... Plt./18

[58] Field of Search ..... Plt. 18, 19

*Primary Examiner*—Howard J. Locker

[57] ABSTRACT

A new rose variety of the Hybrid Tea class, characterized by its continuous and profuse production of large and distinct pink flowers, borne singly on very strong upright stems on a sturdy bush of medium height, having abundant foliage.

2 Drawing Sheets

BACKGROUND OF THE INVENTION

The present invention relates to a new and distinct variety of rose plant of the hybrid tea class. Which was originated by me by crossing the variety "Tineke" (U.S. Plant Pat. No. 8,055) with an unnamed (SR 85.055) and unpatented seedling.

Tineke differs from "Selvanadum" by its white flower color, longer stems, and shorter vase life.

The primary objective of this breeding was to obtain a new rose variety comparable to that of "Tineke", but which bears pink flowers. While the results achieved a distinct pink hybrid tea rose of large size, the new variety did not other wise correspond to the characteristics of "Tineke", but nevertheless, achieved a new and distinct combination of characteristics which is desirable and attractive, as well as different from anything heretofore available, as evidenced by the following characteristics which are outstanding in the new variety:

(1) a large distinct pink flower
(2) rapid flowering cycles
(3) an abundant foliage
(4) a vigorous upright plant.
(5) a plant which has many thorns on the stems The foregoing characteristics and distinctions definitely differentiate the new variety from its parents, as well as from all other varieties of which I am aware, and asexual reproduction of the new variety by cuttings, grafting or tissue culture as performed in a greenhouse in De Kwakel, the Netherlands, shows that these and all other characteristics and distinctions come true to form and are established and transmitted through succeeding propagations.

BRIEF DESCRIPTION OF THE DRAWINGS

The new variety of rose plant is illustrated by the accompanying photographic illustrations, of which:

Sheet 1 shows a full face view of the flower and

Sheet 2 shows typical specimens of the vegetative growth and flowers of the new variety in different stages of development. The color renditions are as nearly true as as it is possible to make same in color illustrations of this character by conventional photographic procedures.

The following is a detailed description of this new variety, with color terminology in accordance with The Royal Horticultural Society Colour Chart (R.H.S.C.C.). The terminology used in the color description herein refers to plate numbers in the aforementioned color chart e.g. "53A" is plate "53A" of The Royal Horticultural Society Colour Chart.

Parentage: Seedling.

*Seed parent.*—"Tineke".

*Pollen parent.*—Unnamed seedling (SR 85.055).

Classification:

*Botanic.*—Hybrid tea.

*Commercial.*—Hybrid tea.

BOTANICAL DESCRIPTION OF THE PLANT

Flower (Observations made from specimens grown in a greenhouse at De Kwakel, the Netherlands)

Blooming habit of Selvanadium: Recurrent-continuous.

A. Bud:

(1) *Size.*—Large. Diameter 2.5–3.0 cm. Length 3.5–4.0 cm.
(2) *Form.*—Egg shaped (oval, pointed); is not affected by wet or hot weather.
(3) *Color.*—When the sepals first divide, the color of the outside is pink 63B at the edges and pink (62B) in the central part of the outer petal.
(4) *Sepals.*—Slightly branched, stand up when petals begin to unfurl. Color: inside: dark green 147A. outside: green 138A.
(5) *Calyx.*—Color: green 143C. Shape: pear. Size: large. Aspect: smooth. Odor when rubbed: none.
(6) *Peduncle.*—Length: long 11 cm. Aspect: smooth. Strength: strong. Color: green 144A.
(7) *Opening.*—Opens up well; is not affected by adverse weather.

B. Bloom:

(1) *Size.*—Large: when fully expanded about 11 cm in diameter with a depth of about 4.5 to 4 cm.
(2) *Borne.*—Single.
(3) *Stems.*—Length: long. Strength: strong.
(4) *Form (when first open).*—Cup formed. Permanence: retains its form.
(5) *Petalage.*—Number of petals: 40–45.
(6) *Color.*—Center of flower: pink (62A–63B). Outer petals: soft pink (63C–64D). Base of petals: yellow (2D). Inside of petals: pink (62A). Reverse of petals: pink (62B). General tonality: pink (62A).

(7) *Discoloration.*—General tonality at end of first day: pink (62A). Second day: pink (62A). Third day: pink (62A).

C. Petals:

(1) *Texture.*—Semi-leathery; not affected by wet or hot weather.

(2) *Appearance.*—Inside: satiny. Outside: shiny.

(3) *Form.*—Round.

(4) *Arrangement.*—Regular.

(5) *Petaloids in center.*—Few; large.

(6) *Persistence.*—Drop off cleanly.

(7) *Fragrance.*—Very weak.

(8) *Lasting quality.*—On the plant — very long. As cut flower —]long (11 days).

Reproductive Organs

Stamens, anthers:

*Size.*—Medium; regularly arranged around styles average number about 120.

*Color.*—Yellow.

Stamens, filaments (threads): Long average about 10 to 12 mm in length.

*Color.*—Yellow.

Pollen:

*Color.*—Yellow.

Styles: Bunched: uneven length; medium (about 5–6 mm) length: thin.

Stigmas:

*Color.*—Yellow.

Ovaries: All enclosed in calyx; funnel-shaped; about 8 mm through center diameter.

Hips/seeds: Seeds are not produced.

Resistancy: Normal resistance against mildew. Californian thrips and red spider mites; More sensitive to white fly.

Plant

Form: Upright and branched.

Growth: Vigorous: upright; average height after one year is 80–100 cm.

Foliage: Compound of 3 to 5 leaflets; average leaflets length is about 5–9 cm; average size of compound leaf is about 16 cm in length; average of 9–10 leaves on main canes.

(1) *Size.*—Medium (2) *Quantity.*—Abundant (3) *Color.*—New foliage: Upper side — green 139A. Under side — green 139C. Old foliage: Upper side — green 139A. Under side — green 139C.

(4) *Shape.*—Oval pointed.

(5) *Texture.*—Upper side — smooth, dull. Under side — smooth, dull.

(6) *Ribs and veins.*—Ordinary.

(7) *Edge.*—Serrated, saw-toothed.

(8) *Serration.*—Single.

(9) *Leaf stem.*—Color: green 143A. Under side: smooth; underside may have 1 or 2 small bent prickles about 2 mm in length.

(10) *Stipules.*—Medium length; smooth.

Wood:

*New wood.*—Color: bronze. Bark: smooth.

*Old wood.*—Color: green. Bark: smooth.

Thorns:

Quantity.—On main stalks from base: many, about 5–7 per 10 cm stem length. On laterals from stalk: many. Form: concave. Length: medium, average length about 14 mm. Hooked: straight. Color (when young): green-bronze. Position: irregular.

Prickles:

*Quantity.*—On main stalks: average. On laterals: average.

Short needles:

*Quantity.*—On main stalks: few. On laterals: few.

I claim:

1. A new and distinct variety of rose plant of the Hybrid Tea class, substantially as herein shown and decribed characterized particularly as to novelty by its continuous production of large, bright pink flowers borne singly on strong, upright stems on a well-foliaged bush of medium height.

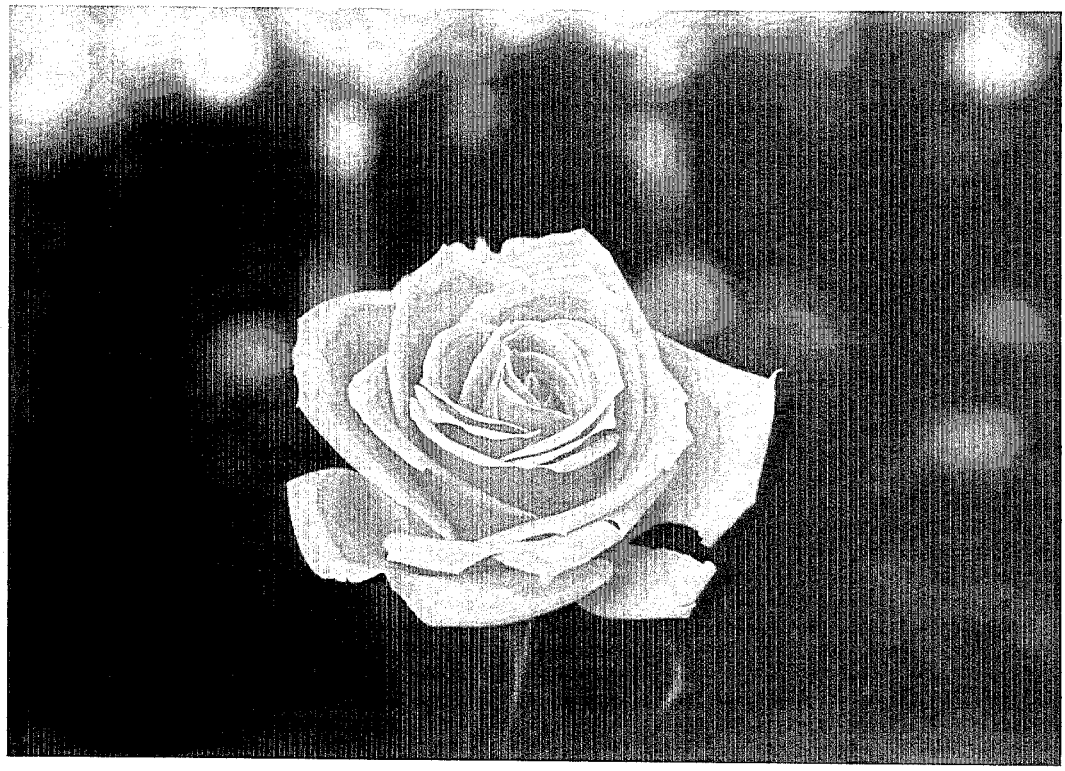

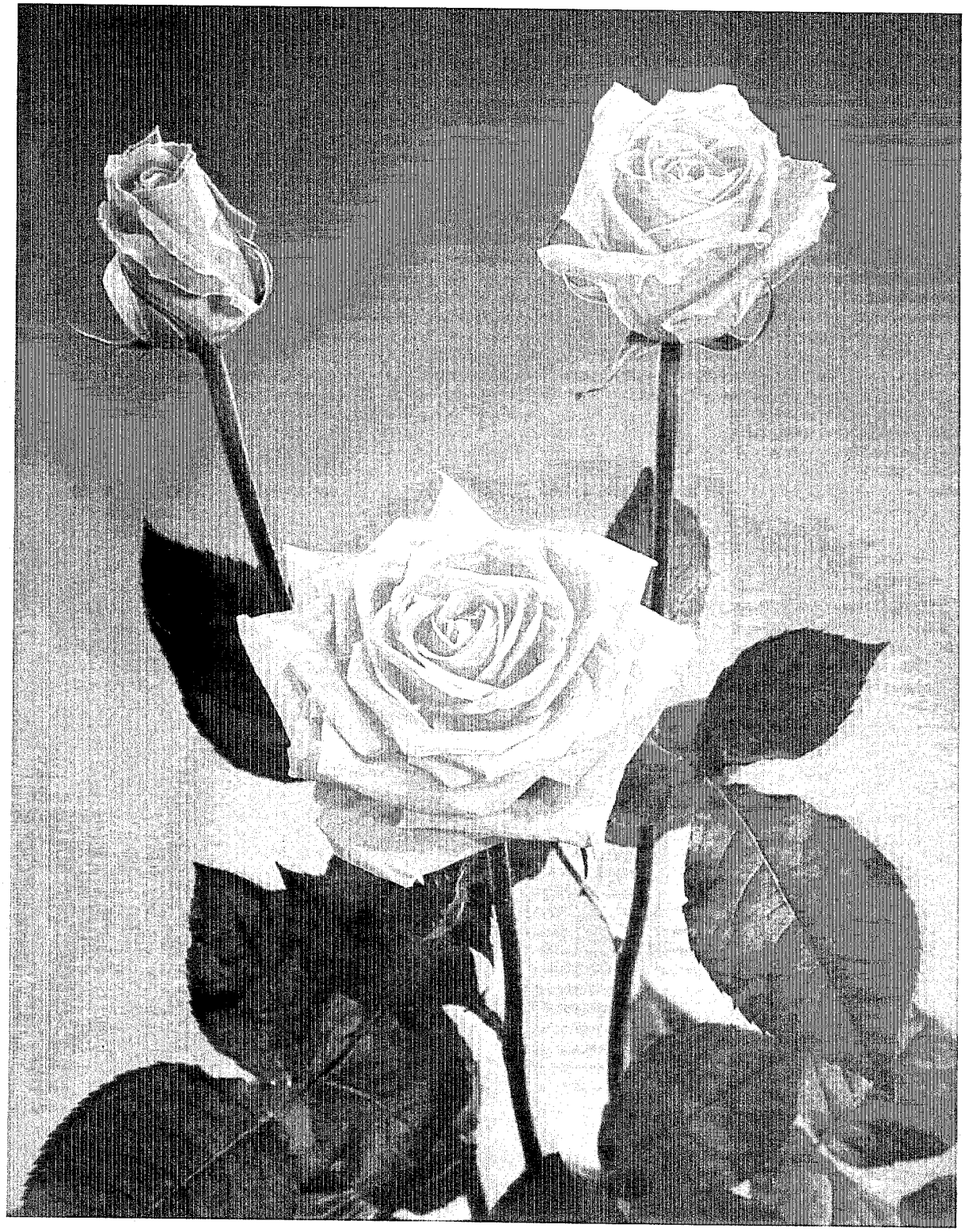

* * * * *